United States Patent [19]

Singer et al.

[11] 3,940,390

[45] Feb. 24, 1976

[54] PROCESS FOR THE PRODUCTION OF 2,3,4,5,6,7-HEXAHYDROCYCLOPENTA-(3)-1,3-OXAZINE-2,4-DIONE COMPOUNDS

[75] Inventors: Rolf Jürgen Singer; Gerhard Jäger, both of Wuppertal, Germany

[73] Assignee: Bayer Aktiengesellschaft, Leverkusen, Germany

[22] Filed: Nov. 28, 1973

[21] Appl. No.: 419,841

[30] Foreign Application Priority Data
Dec. 13, 1972 Germany............................ 2260859

[52] U.S. Cl............................................ 260/244 R
[51] Int. Cl.² ......... C07D 265/00; C07D 273/00; C07D 295/00
[58] Field of Search ................................... 260/244

[56] References Cited

UNITED STATES PATENTS 3,725,402 4/1973 Disselkotter .................... 260/244 R

FOREIGN PATENTS OR APPLICATIONS 1,957,312 3/1971 Germany

Primary Examiner—Sam Rosen
Assistant Examiner—D. W. Robinson
Attorney, Agent, or Firm—Burgess, Dinklage & Sprung

[57] ABSTRACT

2, 3, 4, 5, 6, 7-hexahydrocyclopenta-[e]-1,3-oxazine-2,4-dione compounds are produced by reacting an adipic acid halide of the formula

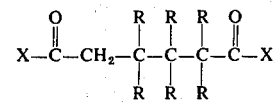

wherein
R is hydrogen or alkyl of up to 3 carbons; and
X is halogen, preferably chlorine or bromine,
with an isocyanate of the formula
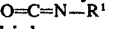
in which
R¹ is hydrocarbyl or substituted hydrocarbyl, preferably of less than 11 carbons. The process is conducted in the presence of a tertiary base, and optionally in the presence of a solvent, at a temperature of from 80° to 180°C., preferably at from 90° to 130°C.

21 Claims, No Drawings

PROCESS FOR THE PRODUCTION OF 2,3,4,5,6,7-HEXAHYDROCYCLOPENTA-(3)-1,3-OXAZINE-2,4-DIONE COMPOUNDS

This invention relates to a process for the preparation of certain 2, 3, 4, 5, 6, 7-hexahydrocyclopenta-[e]-1,3-oxazine-2,4-dione compounds. Such compounds are useful as intermediates in the synthesis of herbicidally effective uracils, for example of 3-cylohexyl-5,6-trimethylene-uracil.

It is known that 2,3,4,5,6,7-hexahydrocyclopenta-[e]-1,3-oxazine-2,4-diones are obtained when 4,5,6,7-tetrahydrocyclopenta-1,3-dioxine-4-ones are heated with isocyanates, optionally in the presence of inert organic solvents, at 80° to 200°C., preferably 120° to 170°C., for a reaction time of up to 30 minutes; see Deutsche Offenlegungsschrift (German Published Specification) 2,005,118. The synthesis of this patent proceeds according to reaction scheme (a);

(a)

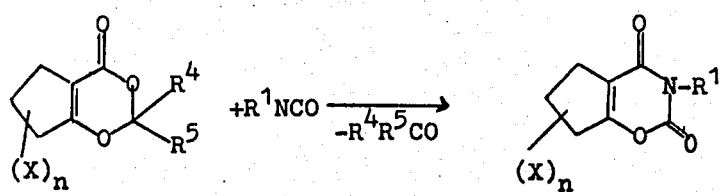

This process, however, exhibits some disadvantages. Thus, it is necessary to remove continuously the carbonyl compound formed in the reaction which means an increased expenditure in terms of apparatus.

Moreover, the starting compounds, tetrahydrocyclopenta-1,3-dioxine-4-ones, must be prepared separately from adipic acid halides and carbonyl compounds in the presence of equivalent amounts of a tertiary amine (see Deutsche Offenlegungsschrift (DOS) 1,957,312).

If isocyanates and adipic acid dihalides are reacted with tertiary amines such as triethylamine or pyridine under the conditions stated in DOS 1,957,312, i.e., at temperatures of −20° to +80°C., our experiments have shown that no cyclization to give 2, 3, 4, 5, 6, 7-hexahydrocyclopenta[e]-1,3-oxazine-2,4-diones according to reaction scheme (b) takes place:

(b)

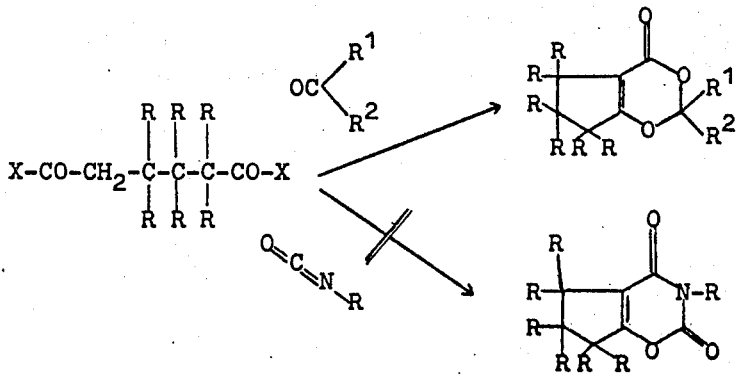

The present invention provides a process for the preparation of a 2, 3, 4, 5, 6, 7-hexahydrocyclopenta[e]-1,3-oxazine-2,4-dione of the general formula

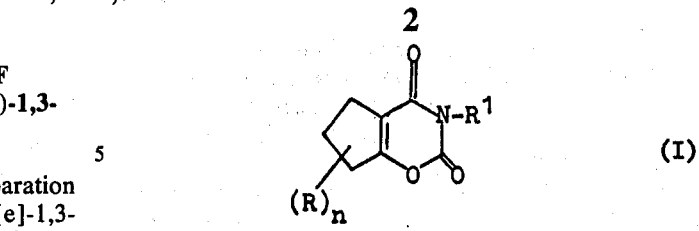

in which
R is alkyl of up to 3 carbon atoms,
$R^1$ is alkyl, optionally substituted cycloalkyl, alkenyl, alkynyl, haloalkyl, alkoxyalkyl, alkylthioalkyl, alkoxycarbonylalkyl, aralkyl, cycloalkyl-alkyl and optionally substituted aryl, preferably, $R^1$ contains not more than 10 carbon atoms; and
n is 0, 1, 2, 3, 4, 5 or 6.

The process of the invention comprises essentially contacting an adipic acid halide of the general formula

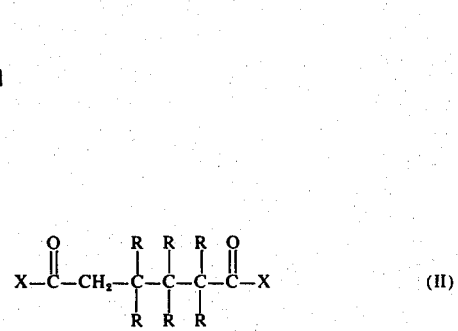

in which
R is hydrogen or alkyl of up to 3 carbon atoms; and
X is halogen, preferably chlorine or bromine, with an isocyanate of the general formula $$O=C=N-R^1 \qquad (III),$$

in which
$R^1$ has the meaning stated above, in the presence of a tertiary base, and optionally in the presence of a solvent, at a temperature of from 80° to 180°C., preferably at from 90° to 130°C.

The compounds of the formula (I) can be prepared by this process in very good yields and good purity.

It is decidedly surprising that by the reaction according to the invention, hexahydrocyclopenta[e]-1,3-oxazine-2,4-diones are formed in very good yields since, in view of the prior art, it had to be expected that the reaction of adipic acid dihalides with isocyanates would not lead to cyclization products.

Preferably, in formula (I), R is methyl or ethyl (most preferably methyl); $n$ is 0, 1, 2 or 3; and $R^1$ is straight-chain or branched alkyl with 1 to 12 carbon atoms (for example, methyl, ethyl, propyl, isopropyl, n-butyl, isobutyl, sec.-butyl, tert.-butyl, pentyl, hexyl, 1,3-dimethylbutyl, 1-methyldecyl or dodecyl), alkenyl or alkynyl with, in either case, 2 to 6 carbon atoms, especially 3 carbon atoms (for example, allyl or propynyl), haloalkyl with 1 to 6 carbon atoms and 1 to 2 halogen atoms, especially chlorine atoms (for example, chloromethyl, 2-chloroethyl, 1-chloroethyl or 6-chlorohexyl), alkoxyalkyl, alkoxycarbonylalkyl or alkylthioalkyl with, in each case, 1 to 6 carbon atoms in the alkyl moiety and 1 to 4 carbon atoms in the alkoxy or alkylthio moiety (for example, methoxymethyl, ethoxymethyl, methoxyethyl, ethoxycarbonylmethyl, n-butoxymethyl, isobutoxycarbonylethyl, isobutoxyethyl, isobutoxymethyl, methylthiomethyl, ethylthiomethyl or n-propylthiomethyl), cycloalkyl with 5 to 8 carbon atoms (for example, cyclopentyl, cyclohexyl, cycloheptyl or cyclooctyl), aryl with 6 to 10 carbon atoms, aralkyl with 6 to 10 carbon atoms in the aryl moiety and 1 to 3 carbon atoms in the optionally branched alkyl moiety, or cyclohexylalkyl with 1 to 4 carbon atoms in the optionally branched alkyl moiety (for example, phenyl, α-naphthyl, β-naphthyl, benzyl, phenethyl, α-methylbenzyl, cyclohexylmethyl or cyclohexylethyl). The phenyl and cyclohexyl radicals $R^1$ can optionally be substituted one or more times by halogen, especially chlorine, or alkyl with up to 3 carbon atoms, especially methyl.

The process according to the invention exhibits a number of advantages. Thus, no intermediate product has to be removed from the reaction solution during the reaction. Moreover, the starting materials of formulas (II) and (III) are, in general, readily obtainable. Also, it is not necessary to prepare, as intermediates, 4, 5, 6, 7-tetrahydrocyclopenta-1,3-dioxine-4-ones according to the method stated in Deutsche Offenlegungsschrift (German Published Specification) 1,957,312 and to prepare from these the oxazine-2,4-diones. An entire reaction step can thus be eliminated, since the same starting materials, namely adipic acid dehalides, are used in the reaction according to the invention.

If adipic acid dichloride and cyclohexylisocyanate are used as starting materials, the reaction course can be represented by the following formula scheme:

described in the literature can be prepared in corresponding manner to the known derivatives; see German Patent 473,960; L. and M. Fieser, Organische Chemie (Organic Chemistry), Verlag Chemie, page 703 (1965); Chem. Ber. 86, 513-518 (1953), 88, 1906-1914 (1955); Liebigs Ann. Chem. 433, 109-111 (1923).

As examples, there may be mentioned:
Adipic acid dichloride,
2,4,4-trimethyladipic acid dichloride,
3-methyladipic acid dichloride,
2-methyladipic acid dichloride, and
3,4,4-trimethyladipic acid dichloride.

The isocyanates of formula (III) are, for the most part, known. The isocyanates that have not yet been described in the literature can be prepared in an analogous manner to the known compounds (see Liebigs Ann. Chem. 562, 75-120 (1949); J. Pharm. Pharmacol. 16(8), 538-548 (1964)).

As examples of the isocyanates (III), there may be mentioned methyl isocyanate, ethyl isocyanate, propyl isocyanate, isopropyl isocyanate, sec.-butyl isocyanate, pentyl isocyanate, n-hexyl isocyanate, dodecyl isocyanate, 1-methyl-decyl isocyanate, 1,3-dimethylbutyl isocyanate, cyclohexyl isocyanate, 3-methylcyclohexyl isocyanate, 4-methylcyclohexyl isocyanate, 2-methylcyclohexyl isocyanate, cyclohexylmethyl isocyanate, 6-chlorohexyl isocyanate, 2-chloroethyl isocyanate, methoxymethyl isocyanate, ethoxycarbonylmethyl isocyanate, n-butoxymethyl isocyanate, isobutoxycarbonylethyl isocyanate, propenyl isocyanate, phenyl isocyanate, 3-chlorophenyl isocyanate, 4-chlorophenyl isocyanate, 3,4-dichlorophenyl isocyanate, benzyl isocyanate, phenylethyl isocyanate, α-methylbenzyl isocyanate, cycloheptyl isocyanate and cyclooctyl isocyanate.

As diluents in the process of this invention, all inert higher-boiling organic solvents are suitable, especially hydrocarbons, such as benzene, toluene or xylenes, chlorinated hydrocarbons, such as chlorobenzene or 1,2-dichlorobenzene, and ethers, such as dibutyl ether.

The reaction according to the present invention is effected in the presence of a tertiary organic base. Examples of such bases are pyridine, α-picoline, β-picoline, γ-picoline, lutidine, collidine, quinoline and N,N-diethylaniline.

The reaction can be carried out not only at normal pressure, but also at elevated pressures. In general, the reaction is carried out at normal pressure, or at 2 to 10 atmospheres gauge in an autoclave.

When carrying out the process according to the invention, for 1 mole of the adipic acid derivative of

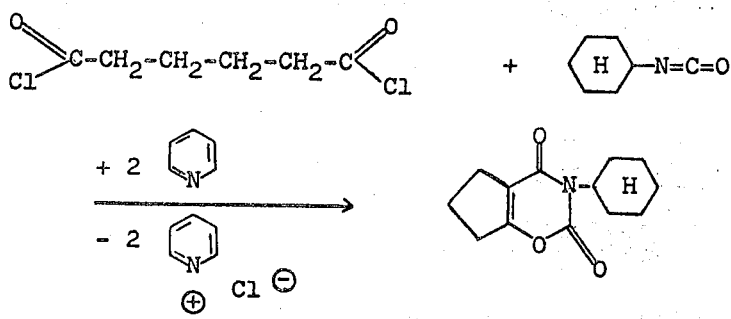

The adipic acid derivatives which can be used according to the invention are for the most part known; the adipic acid derivatives that have not hitherto been formula (II), there are generally used 1-1.4 moles of the isocyanate of formula (III) and an equivalent amount (2 moles) of an acid-binder.

To isolate the compounds of formula (I), the halide formed is filtered off, the solvent is distilled off and the residue is purified in customary manner, for example by recrystallization or by distillation by rectification.

A number of the 2,3,4,5,6,7-hexahydrocyclopenta[e]-1,3-oxazine-2,4-diones which can be prepared according to the invention are known; see DOS 2,005,118; others form the subject matter of U.S. Pat. Applications Ser. No. 266,872, filed June 28, 1972, Ser. No. 266,877, filed June 28, 1972 and Ser. No. 330,524, filed Feb. 7, 1973.

The process of this invention is illustrated in the following Examples.

EXAMPLE 1

Preparation of
3-cyclohexyl-2,3,4,5,6,7-hexahydrocyclopenta[e]-1,3-oxazine-2,4-dione

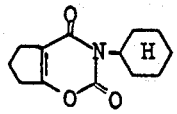

With good stirring and reflux cooling, 732 g (4 moles) of adipic acid dichloride were added dropwise in 45 minutes to a solution (which had been heated to 120°C.) of 751.2 g (6 moles) of cyclohexylisocyanate and 648 ml (8 moles) of pyridine in 1.5 l of xylene. After three hours' stirring at 120°C., the reaction mixture was cooled to 10°C., filtered off from the separated pyridine hydrochloride, and the precipitate was washed twice with, in each case, 200 ml of xylene. The filtrate was freed from solvent under reduced pressure until dryness; the residue was boiled up with 4 l of ligroin, filtered and the filtrate was concentrated. On cooling, a precipitate was obtained which was dissolved in 75% strength aqueous methanol, cooled to 0°C. and precipitated by addition of water.

810 g (86.5% of the theory) of 3-cyclohexyl-2,3,4,5,6,7-hexahydrocyclopenta[e]-1,3-oxazine-2,4-dione of the melting point 72° to 74°C. were obtained. The product was sufficiently pure for further processing.

On recrystallization of a sample from ligroin, the melting point rose to 80° to 82°C.

With the use of the following bases instead of pyridine the yield changed as follows:

| Base | Yield of 3-Cyclohexyl-2,3,4,5,6,7-hexahydro-cyclopenta[e]-1,3-oxazine-2,4-dione (% of the theory) |
|---|---|
| 2-methylpyridine | 56 |
| 4-methylpyridine | 47 |
| quinoline | 59 |
| tributylamine | 39 |
| N,N-dimethylaniline | 19 |
| N-methylpyrrolidine | 19 |
| (compare:pyridine | 86.5) |

EXAMPLE 2

Preparation of
3-cyclooctyl-2,3,4,5,6,7-hexahydrocyclopenta[e]-1,3-oxazine-2,4-dione

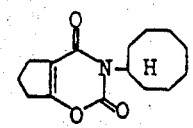

With stirring and reflux cooling, 183 g (1 mole) of adipic acid chloride were added to a solution, kept at 120°C., of 168.6 g (1.1 moles) of cyclooctylisocyanate and 162 ml (2 moles) of pyridine in 500 ml of xylene. After 3 hours' reaction time, cooling was effected, followed by filtering off from the separated pyridine hydrochloride. The filtrate was first freed from solvent under reduced pressure and, finally, was distilled in a high vacuum. 158.2 g (60% of the theory) of 3-cyclooctyl-2,3,4,5,6,7-hexahydrocyclopenta[e]-1,3-oxazine-2,4-dione of the boiling point 172°–174°C/0.3 mm Hg were obtained when solidified to give a colorless crystal mass of the melting point 48°–51°C.

In an analogous manner, the compounds listed in Table 1 were prepared:

Table 1

| Example No. | R | n | R¹ | Melting point °C | Boiling point mm/°C | Refractive index |
|---|---|---|---|---|---|---|
| 3 | — | 0 | cyclohexyl-H | 45–47 | 0.05/143 | — |
| 4 | — | 0 | CH₃-cyclohexyl-H | 91–92 | — | — |
| 5 | — | 0 | cyclohexyl-H (CH₃) | — | 0.8/176 | — |

Table 1-continued

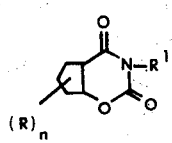

| Example No. | R | n | R[1] | Melting point °C | Boiling point mm/°C | Refractive index |
|---|---|---|---|---|---|---|
| 6 | — | 0 | $CH_3$ | — | 0.2/107 | — |
| 7 | — | 0 | $C_2H_5$ | — | 0.6/108 | — |
| 8 | — | 0 | $C_3H_7$ | — | 0.9/142 | — |
| 9 | — | 0 | $CH(CH_3)_2$ | — | 0.6/137 | — |
| 10 | — | 0 | $C_4H_9$ | — | 0.2/116 | — |
| 11 | — | 0 | $(CH_3)_2CH-CH_2$ | — | 0.2/144 | — |
| 12 | — | 0 | $C_2H_5-CH(CH_3)-$ | — | 1/143 | — |
| 13 | — | 0 | $(CH_3)_2CH-CH_2-CH(CH_3)-$ | — | 1/146 | — |
| 14 | — | 0 | $C_9H_{19}-CH(CH_3)-$ | — | 0.5/180 | — |
| 15 | — | 0 | $CH_3-(CH_2)_{11}-$ | 35–38 | 0.3/198 | — |
| 16 | 5-$CH_3$ 6-$CH_3$ (1:1 mixture) | 1 | $(CH_3)_2CH-CH_2$ | — | 0.3/138 | — |
| 17 | — | 0 | $ClC_2H_4$ | — | 0.3/159 | — |
| 18 | — | 0 | $ClC_6H_{12}$ | — | 0.9/195 | — |
| 19 | — | 0 | $CH_3OCH_2$ | — | 0.2/176 | — |
| 20 | — | 0 | $n$-$C_4H_9OCH_2$ | — | 0.4/149 | — |
| 21 | — | 0 | $C_2H_5-OCOCH_2$ | — | — | $n_D^{20}$: 1.5064 |
| 22 | — | 0 | $(CH_3)_2CH-CH_2OCO-C_2H_4$ | — | 0.2/182 | — |
| 23 | — | 0 | $CH_2=CH-CH_2$ | — | 0.7/134 | — |
| 24 | — | 0 | cyclohexyl-$CH_2$ | 50–52 | 0.25/153 | — |
| 25 | 5-$CH_3$ 6-$CH_3$ (1:1 mixture) | 1 | cyclohexyl | — | 0.2/163 | — |
| 26 | 5-$CH_3$ 6-$CH_3$ (1:1 mixture) | 1 | $CH_3$-cyclohexyl | — | 0.2/153 | — |
| 27 | 5,7,7-$(CH_3)$ | 3 | cyclohexyl | — | 0.2/144 | — |
| 28 | — | 0 | $CH_3-(CH_2)_{10}-CH(CH_3)$ | — | — | $n_D^{20}$: 1.4897 |
| 29 | — | 0 | 2-methylcyclohexyl | — | 0.7/178 | — |
| 30 | — | 0 | 3-chlorophenyl | 155–156 | — | — |
| 31 | — | 0 | 4-chlorophenyl | 139–140 | — | — |
| 32 | — | 0 | 3,4-dichlorophenyl | 190–191 | — | — |
| 33 | — | 0 | phenyl-$CH_2$ | 83–84.5 | 0.4/185 | — |
| 34 | — | 0 | phenyl-$C_2H_4$ | 115–116 | — | — |
| 35 | — | 0 | phenyl-$CH(CH_3)$ | — | 0.5/180 | — |

Table 1-continued

| Example No. | R | n | R¹ | Melting point °C | Boiling point mm/°C | Refractive index |
|---|---|---|---|---|---|---|
| 36 | 5-$CH_3$ 6-$CH_3$ (1:1 mixture) | 1 | phenyl | 116–117 | — | — |
| 37 | — | 0 | phenyl | 145–146 | — | — |

Reaction of
3-cyclohexyl-2,3,4,5,6,7-hexahydrocyclopenta[e]-1,3-oxazine-2,4-dione with ammonia, with formation of the corresponding uracil

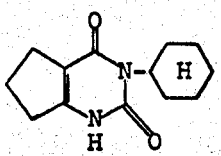

Dry ammonia gas was introduced for 1 hours, with ice cooling, into a solution of 117.8 g (0.5 mole) of 3-cyclohexyl-2,3,4,5,6,7-hexahydrocyclopenta[e]-1,3-oxazine-2,4-dione (prepared according to Example 1) in isopropanol (500 ml). Thereafter, the reaction mixture was brought to room temperature and the excess ammonia was removed by gentle warming. 300 ml of 20%-strength aqueous hydrochloride acid were added to the reaction solution which was then heated at 50° to 60°C. for 30 minutes and then cooled to room temperature. After some time a crystalline precipitate formed which was filtered and dried.

There were so obtained 112.5 g (95% of the theory) of 3-cyclohexyl-5,6-trimethylene-uracil of the melting point 315°–316°C.

Example of the preparation of α,α-dimethyladipic acid chloride

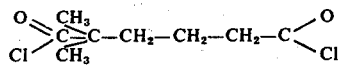

a. α,α-dimethyl-δ-chlorovaleric acid nitrile.

The reaction was carried out in a nitrogen atmosphere; mercury valves were used. To an ethereal solution of phenyllithium, prepared from 24.4 g (3.5 g-atoms) of lithium and 283 g (1.8 moles) of bromobenzene, there were added, at 10°–15°C., 112 g (1.64 moles) of diethylamine and, 15 minutes later, 116 g (1.68 moles) of isobutyronitrile. The mixture was stirred for a further 20 minutes at room temperature, then it was forced into a dropping funnel with nitrogen. From there it was added dropwise at 0°–5°C. to a solution of 356 g (2.26 moles) of 1,3-bromochloropropane in 600 ml of absolute ether. Subsequently, stirring was effected for a further 3 hours at boiling temperature. Thereafter, water was added, with cooling; the ether phase was separated and the aqueous phase was several times extracted with ether. The ether extracts were washed first with dilute sulfuric acid and then with water, dried with sodium sulfate and distilled. The total yield was 397.3 g (=2.73 moles = 81% of the theory with reference to the isobutyronitrile used) of the boiling point 92°–98°C/10 mm Hg (see J.Org.Chemistry 27, 2827 (1962)).

b. α,α-dimethyladipic acid dinitrile

To a suspension of 160.7 g (3.28 moles) of sodium cyanide in 500 ml of dimethyl formamide there was added dropwise at 110°–115°C., with intensive stirring, a solution of 397.3 g (2.73 moles) of α,α-dimethyl-G-chlorovaleric acid nitrile in 350 ml of dimethyl formamide. Subsequently, stirring was effected for a further 3 hours; the internal temperature was slowly increased to 135°C. After cooling, 2 liters of water were added and extraction with ether was effected several times. The ether extracts were dried over sodium sulfate and distilled over a packed column. 326 g (= 2.39 moles = 87.5%) of the boiling point 101°–102°C/0.5 mm Hg were obtained (see J.Org. Chemistry 27, 2827 (1962).

c. α,α-dimethyladipic acid

After 6 hours' reflux boiling of a mixture of 158 g (1 mole) of α,α-dimethyladipic acid dinitrile in a 3:1 mixture of alcohol and conc. hydrochloric acid, 157 g (90% of the theory) of α,α-dimethyladipic acid of the melting point 88°–91°C. were obtained.

d. α,α-dimethyladipic acid dichloride 87 g (0.5 mole) of α,α-dimethyladipic acid were dissolved in 500 ml of anhydrous benzene, a 10% molar excess of thionyl chloride was added and heating to a boil under reflux was effected for 4 hours. After completion of the reaction, first the solvent was removed in a vacuum then the residue was distilled. 94 g (90% of

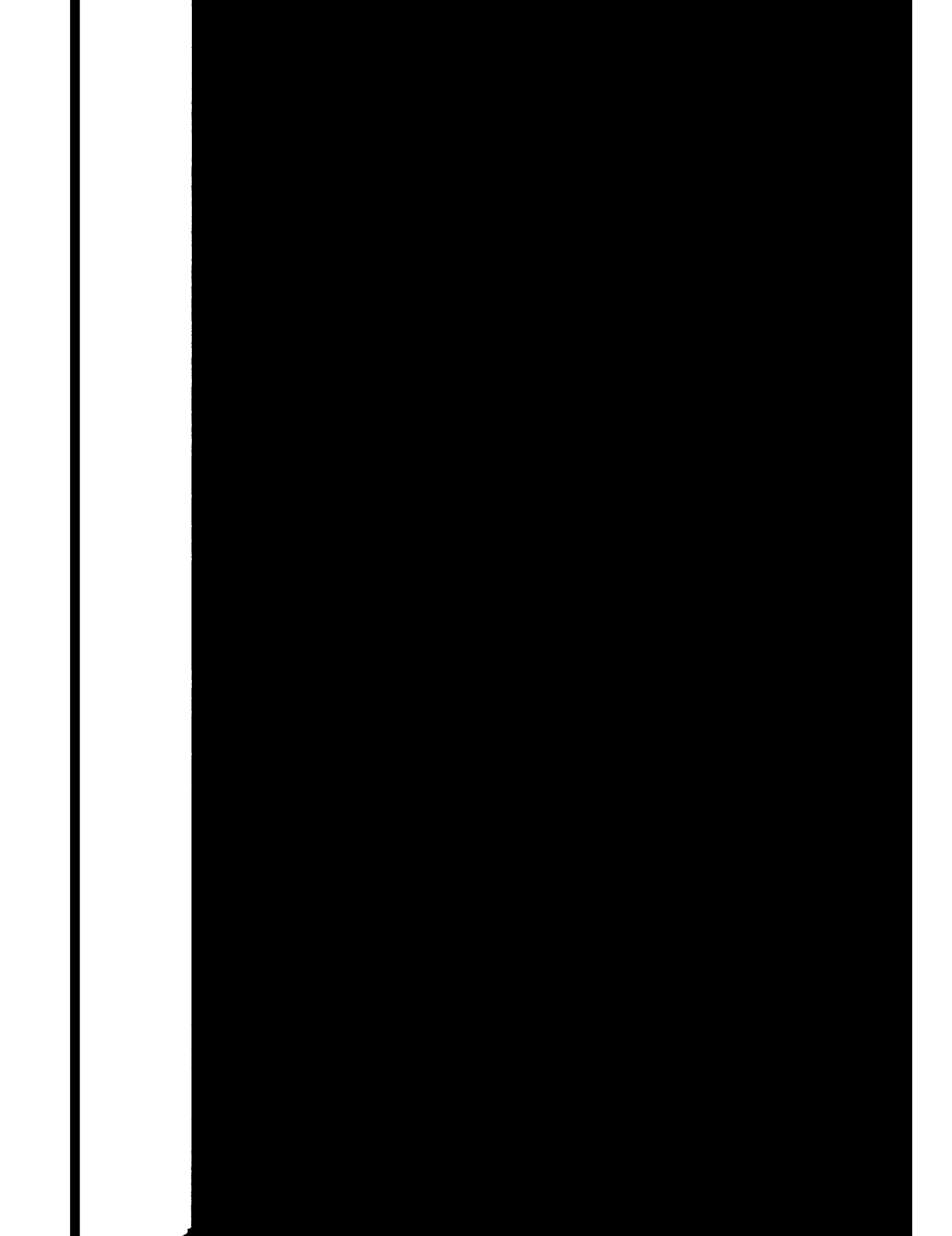

UNITED STATES PATENT AND TRADEMARK OFFICE
CERTIFICATE OF CORRECTION

PATENT NO. : 3,940,390
DATED : February 24, 1976
INVENTOR(S) : Rolf Jürgen Singer et al It is certified that error appears in the above—identified patent and that said Letters Patent are hereby corrected as shown below:

Column 9, line 41, cancel "hours" and substitute -- hour --.

Column 10, line 46, cancel "G" and substitute -- o --.

Column 12, line 26, Claim 7, after "chlorine" insert -- , --.

Signed and Sealed this twenty-second Day of June 1976

[SEAL]

Attest:

RUTH C. MASON
*Attesting Officer*

C. MARSHALL DANN
*Commissioner of Patents and Trademarks*